United States Patent [19]
Turski et al.

[11] Patent Number: 5,614,509
[45] Date of Patent: Mar. 25, 1997

[54] PHARMACEUTICAL AGENTS FOR PREVENTING THE DEVELOPMENT OF TOLERANCE DURING THE TREATMENT WITH BENZODIAZEPINE-RECEPTOR-BINDING ACTIVE INGREDIENTS

[75] Inventors: Lechoslaw Turski; Karin G. Steppuhn; Herbert Schneider; David N. Stephens, all of Berlin, Germany

[73] Assignee: Schering Aktiengesellschaft, Berlin, Germany

[21] Appl. No.: 367,129

[22] PCT Filed: Jun. 22, 1993

[86] PCT No.: PCT/DE93/00561

§ 371 Date: Mar. 2, 1995

§ 102(e) Date: Mar. 2, 1995

[87] PCT Pub. No.: WO94/01094

PCT Pub. Date: Jan. 20, 1994

[30] Foreign Application Priority Data

Jul. 9, 1992 [DE] Germany ............ 42 22 826.3

[51] Int. Cl.⁶ .......... A61K 31/675; A61K 31/66; A61K 31/47; A61K 31/445; A61K 31/41; A61K 31/40; A61K 31/135; A61K 31/13

[52] U.S. Cl. .......... 514/82; 514/85; 514/89; 514/93; 514/114; 514/120; 514/220; 514/221; 514/289; 514/312; 514/317; 514/383; 514/425; 514/647; 514/662; 514/674

[58] Field of Search ........... 514/120, 85, 89, 514/93, 289, 662, 647, 674, 425, 317, 312, 221, 220, 114, 82, 383

[56] References Cited

U.S. PATENT DOCUMENTS 5,474,990  12/1995  Olney .................. 514/226.2

FOREIGN PATENT DOCUMENTS 0488959  6/1992  European Pat. Off. .
0514023  11/1992  European Pat. Off. .
0527540  2/1993  European Pat. Off. .
0530446  3/1993  European Pat. Off. .

OTHER PUBLICATIONS

The Merek Manual, 15th edition, 1987, pp. 1476–1495.
Khanna et al, *Chemical Abstracts*, vol. 116, No. 23, abstract No. 230028h, 1992, p. 278.

*Primary Examiner*—Marianne M. Cintins
*Assistant Examiner*—William R. A. Jarvis
*Attorney, Agent, or Firm*—Millen, White, Zelano, & Branigan, P.C.

[57] ABSTRACT

The use of NMDA receptor antagonists or their physiologically compatible salts for preventing the development of tolerance during the long-term treatment with benzodiazepine-receptor-binding active ingredients as well as the combination of new pharmaceutical agents with benzodiazepine-receptor-binding active ingredients is described.

10 Claims, 1 Drawing Sheet

PHARMACEUTICAL AGENTS FOR PREVENTING THE DEVELOPMENT OF TOLERANCE DURING THE TREATMENT WITH BENZODIAZEPINE-RECEPTOR-BINDING ACTIVE INGREDIENTS

The invention relates to the use of NMDA antagonists or their physiological salts for the production of pharmaceutical agents for preventing the development of tolerance during the treatment with benzodiazepine-receptor-binding active ingredients as well as for the suppression of dependence.

Both in clinical studies and in practice, long-term treatments with benzodiazepine-receptor-binding pharmaceutical agents, such as, e.g., diazepam (valium) are frequently performed in the case of convulsive disorders and sleep disturbances or for sedation and anxiolytic purposes. The greatest problem for the patients is the tolerance occurring during the treatment and the withdrawal symptoms occurring after these substances are discontinued, such as muscular stiffness, tremors, cramps and states of anxiety, under which the patients suffer.

The role of excitatory amino acids in the central nervous system has received increasing interest in recent years. Glutamate thus was identified as a neurotransmitter and three other receptor subtypes have been found and characterized for excitatory amino acids, which were named according to the specifically effective glutamate-analogous amino acids N-methyl-D-aspartate (NMDA), kainate and quisqualate receptors.

Surprisingly, it has been found that excitatory amino acids are involved in the development of tolerance relative to benzodiazepine-receptor-binding active ingredients and that the blocking of the NMDA receptor prevents or reduces the development of tolerance.

The object of the invention is the use of NMDA antagonists or their physiologically compatible salts for the production of pharmaceutical agents for preventing the development of tolerance, which results during the treatment with benzodiazepine-receptor-binding active ingredients.

BRIEF DESCRIPTION OF THE DRAWING

Various other objects, features and attendant advantages of the present invention will be more fully appreciated as the same becomes better understood when considered in conjunction with the accompanying drawing, wherein.

Figure 1:
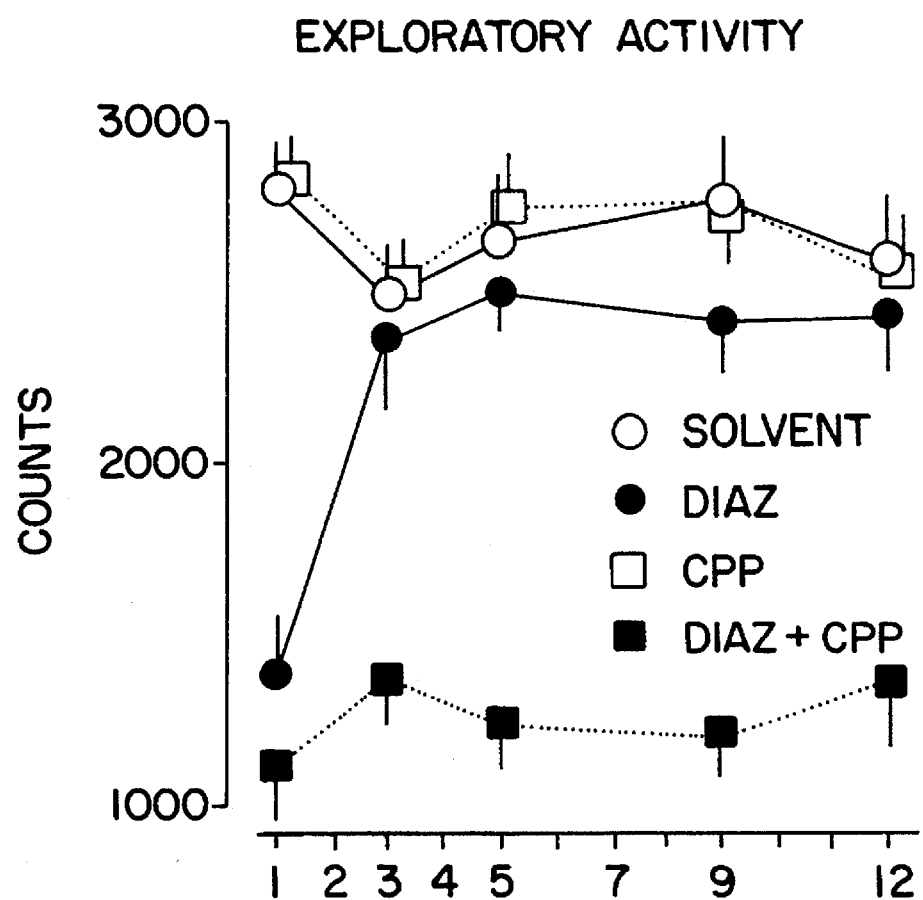
FIG. 1 shows the amount of exploratory activity (COUNTS) in mice treated s.c. for 12 days with diazepam in sesame oil (DIAZ), sesame oil alone (SOLVENT), the competitive NMDA antagonist 3-(($\pm$)2-carboxy-piperazin-4-yl)-propyl-1-phosphonic acid (CPP), and diazepam and CPP together (DIAZ+CPP). The amount of exploratory activity shows the sedative effect of diazepam; treatment with diazepam at first causes sedation, which is abolished by the development of tolerance; co-treatment with CPP prevents the development of tolerance.

The methods for determining the tolerance are based on the measurement of the exploratory locomotor activity in mice during long-term treatment with BDZ-receptor-binding active ingredients, as is shown by the example of benzodiazepines.

The suppression of the exploratory activity is part of the most known sedative effects. During long-term treatment with BDZ, a loss of the sedative effect takes place in mice.

To examine the development of tolerance during the long-term administration of benzodiazepines, male NMRI mice weighing 20–24 g were treated under daily controlled conditions (0600–1800 hours of a light/dark cycle, 45–55% atmospheric humidity and free access to water and food) for 12 days with 15 mg/kg of diazepam in sesame oil. The control animals were treated subcutaneously with the vehicle under the same conditions for 12 days. In the case of mice, the 12-day treatment with 15 mg/kg of diazepam results in a total tolerance in the sedative property.

To examine the role of the excitatory amino acids in the development of tolerance, the animals were treated with NMDA antagonists. In this case, minipumps having an osmotic effect were implanted intraperitoneally under a slight ether anesthesia and the behavior of mice in the locomotion unit was examined from day one to day twelve. The pumps were filled in advance with NMDA antagonists. The pumping rate was 1 mg/kg/h over 12 days.

The development of tolerance is prevented by the treatment with NMDA antagonists during the administration of diazepam, as is shown by the example with CPP (FIG. 1).

These studies show that the blocking of the NMDA receptor during the treatment with BDZ-binding active ingredients is sufficient to prevent the development of tolerance in the sedative effect.

Suitable are, according to the invention:

The competitive NMDA antagonists-2-amino-7-phosphonoheptanoic acid (AP 7) and analogs; 3-(($\pm$)2-carboxy-piperazin-4-yl)-propyl-1-phosphonic acid (CPP) and analogs; (e)-4-(3-phosphonoprop-2-enyl)piperazine-2-carboxylic acid (CPPenes) and analogs; cis-4-phosphonomethyl-2-piperidinecarboxylic acid (CGS 19755); DL-(E)-2-amino-4-methyl-5-phosphono-3-pentanoic acid, (CGP 40115);

enantiomers and analogs;

S-$\alpha$-amino-5-phosphonomethyl-[1,1'-biphenyl]-3-propanoic acid,

E-2-amino-4-methyl-5-phosphono-3-pentenoic acid,

E-2-amino-4-methyl-5-phosphono-3-pentenoic acid ethyl ester, cis-4-phosphonomethyl-2-piperidinecarboxYlic acid, (R)-4-oxo-2-amino-5-phosphono-pentanoic acid, 2-amino-4,5-(1,2-cyclohexyl)-7-phosphonoheptanoic acid, 4-(phosphonomethyl)-DL-phenylglycine, 4-(3-phosphonopropyl)-2-piperidinecarboxylic acid, 2-(2-phosphonoethyl)-DL-phenylalanine, 3-carboxy-5-(phosphonoethyl)-1,2,3,4-tetrahydroisoquinoline, 3-carboxy-5-phosphono-1,2,3,4-tetrahydroisoquinoline, cis-DL-4-[(1(2)H-tetrazol-5-yl)methyl]2-piperidinecarboxylic acid, cis-4-(3-phosphonoprop-1-enyl)-2-piperidinecarboxylic acid, E-2-amino-4-propyl-5-phosphono-3-pentenoic acid, phosphoric acid-4-(2-carboxy-piperidinyl)ester and 1-[4(4-chloro-$\alpha,\alpha$-dimethylbenzyl)-2-methoxyphenyl]-1,2,4-triazole-3-carboxylic acid amide;

Noncompetitive MMDA antagonists (+)10,11-dihydro-5-methyl-5H-dibenzo-[a,d]cycloheptane-5,10-imine (MK-801) and analogs; memantines and other amantadine analogs; ketamine and analogs, budipine and analogs; ifenprodil and analogs; antagonists of the glycine binding site— kynurenic acid and analogs; 1-hydroxy-3-aminopyrrolidin-2-one (HA-966) and analogs; polyamines spermine and spermidine and analogs: inhibitors of the excitatory amino acid synthesis.

Competitive NMDA antagonists can be considered preferable.

As benzodiazepine-receptor-binding active ingredients, benzodiazepines and β-carbolines can be mentioned, such as, for example, diazepam, nitrazepam, triazolam, chlordiazepoxide.

This invention also comprises the combination of NMDA antagonists or their salts with benzodiazepine-binding active ingredients to prevent the development of tolerance in treatment with sedative substances.

The invention also comprises pharmaceutical agents, which contain the above-mentioned compounds in an effective amount, their production as well as the use of the compounds for the production of pharmaceutical agents for prophylaxis of the development of tolerance in BDZ-receptor-binding active ingredients. The pharmaceutical agents are produced according to processes known in the art, by the active ingredient being brought with suitable vehicles, adjuvants and/or additives into the form of a pharmaceutical preparation, which is especially suitable for enteral or parenteral administration.

The administration can take place orally or sublingually as solid in the form of capsules or tablets or as liquid in the form of solutions, suspensions, elixirs or emulsions or rectally in the form of suppositories or in the form of injection solutions optionally also usable subcutaneously. As adjuvants for the desired pharmaceutical agent formulation, the inert organic and inorganic vehicle materials known to one skilled in the art are suitable, such as, for example, water, gelatin, gum arabic, lactose, starch, magnesium stearate, talc, vegetable oils, polyalkylene glycols, etc. Moreover, preservatives, stabilizers, wetting agents, emulsifiers or salts optionally can be contained to change the osmotic pressure or buffer.

The pharmaceutical preparations can be present in solid form, for example, as tablets, coated tablets, suppositories, capsules or in liquid form, for example, as solutions, suspensions or emulsions or formulated as depot preparation.

As vehicle systems, interface-near adjuvants, such as salts of the bile acids or animal or plant phospholipids, but also their mixtures as well as liposomes or their components, can also be used.

For oral use, especially tablets, coated tablets or capsules with talcum and/or hydrocarbon vehicles or binders, such as, for example, lactose, corn or potato starch, are suitable. The use can also take place in liquid form, such as, for example, as juice, to which optionally a sweetener is added.

The dosage of the active ingredients can vary depending on the method of administration, age and weight of the patient, type and severity of the disease to be treated and similar factors. The daily dose is 0.001–0.034 mg, and the dose can be given as a single dose to be administered one time or subdivided into 2 or more daily doses.

In the combination preparations according to the invention, the active ingredients can be present in one formulation or else in respectively separate formulations, and the entire dose is administered one time or is divided into several doses.

We claim:

1. A method of preventing the development of tolerance for benzodiazepine-receptor-binding active agents in a patient in need of treatment with such active agents, comprising administering an effective amount of an NMDA antagonist or a physiologically compatible salt thereof.

2. A method of claim 1, wherein the, NMDA antagonist or a physiologically compatible salt thereof is administered together with a benzodiazepine-receptor-binding active agent.

3. A method of claim 1, wherein the NMDA antagonist is a competitive NMDA antagonist or a noncompetitive NMDA antagonist.

4. A method of claim 1, wherein the NMDA antagonist is a competitive NMDA antagonist.

5. A method of claim 1, wherein the NMDA antagonist is a noncompetitive NMDA antagonist.

6. A method of claim 5, wherein the noncompetitive NMDA antagonist is an antagonist of the glycine binding site or an inhibitor of excitatory amino acid synthesis.

7. A method of claim 4, wherein the competitive NMDA antagonist or a physiologically compatible salt thereof is selected from 2-amino-7-phosphonoheptanoic acid;

3-((±)2-carboxy-piperazin-4-yl)propyl-1-phosphonic acid;

(e)-4-(3-phosphonoprop-2-enyl)piperazine-2-carboxylic acid;

cis-4-phosphonomethyl-2-piperidinecarboxylic acid;

DL-(E)-2-amino-4-methyl-5-phosphono-3-pentanoic acid;

S-α-amino-5-phosphonomethyl-[1,1'-biphenyl]-3-propanoic acid;

E-2-amino-4-methyl-5-phosphono-3-pentenoic acid;

E-2-amino-4-methyl-5-phosphono-3-pentenoic acid ethyl ester;

cis-4-phosphonomethyl-2-piperidinecarboxylic acid;

(R)-4-oxo-2-amino-5-phosphono-pentanoic acid;

2-amino-4,5-(1,2-cyclohexyl)-7-phosphonoheptanoic acid;

4-(phosphonomethyl)-DL-phenylglycine;

4-(3-phosphonopropyl)-2-piperidinecarboxylic acid;

2-(2-phosphonoethyl)-DL-phenylalanine;

3-carboxy-5-(phosphonoethyl)-1,2,3,4-tetrahydroisoquinoline;

3-carboxy-5-phosphono-1,2,3,4-tetrahydroisoquinoline;

cis-DL-4-[(1(2)H-tetrazol-5-yl)methyl]2-piperidinecarboxylic acid;

cis-4-(3-phosphonoprop-1-enyl)-2-piperidinecarboxylic acid;

E-2-amino-4-propyl-5-phosphono-3-pentenoic acid;

phosphoric acid-4-(2-carboxy-piperidinyl)ester; and

1-[4(4-chloro-α,α-dimethylbenzyl)-2-methoxyphenyl]-1,2,4-triazole-3-carboxylic acid amide.

8. A method of claim 5, wherein the noncompetitive NMDA antagonist or a physiologically compatible salt thereof is selected from (+) 10,11-dihydro-5-methyl-5H-dibenzo-[a,d]cycloheptane-5,10-imine;

a memantine;

ketamine;

budipine; and ifenprodil.

9. A method of claim 6, wherein the noncompetitive NMDA antagonist or a physiologically compatible salt thereof is an antagonist of the glycine binding site selected from kynurenic acid and 1-hydroxy-3-aminopyrrolidin-2-one.

10. A method of claim 6, wherein the noncompetitive NMDA antagonist or a physiologically compatible salt thereof is an inhibitor of excitatory amino acid synthesis selected from spermine and spermidine.

* * * * *